US011580636B2

(12) United States Patent
Wang (10) Patent No.: US 11,580,636 B2
(45) Date of Patent: *Feb. 14, 2023

(54) AUTOMATIC GRAPH SCORING FOR NEUROPSYCHOLOGICAL ASSESSMENTS

(71) Applicant: Pearson Education, Inc., Bloomington, MN (US)

(72) Inventor: Zhaodong Wang, San Carlos, CA (US)

(73) Assignee: PEARSON EDUCATION, INC., Bloomington, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/953,150

(22) Filed: Nov. 19, 2020

(65) Prior Publication Data

US 2021/0073981 A1 Mar. 11, 2021

Related U.S. Application Data

(63) Continuation of application No. 16/373,079, filed on Apr. 2, 2019, now Pat. No. 10,872,412.

(60) Provisional application No. 62/651,472, filed on Apr. 2, 2018.

(51) Int. Cl.
| | |
|---|---|
| *G06T 7/00* | (2017.01) |
| *G06T 3/40* | (2006.01) |
| *G06K 9/62* | (2022.01) |
| *G09B 19/00* | (2006.01) |
| *A61B 5/00* | (2006.01) |

(52) U.S. Cl.
CPC .......... *G06T 7/0012* (2013.01); *A61B 5/4088* (2013.01); *G06K 9/628* (2013.01); *G06K 9/6261* (2013.01); *G06K 9/6262* (2013.01); *G06K 9/6287* (2013.01); *G06T 3/40* (2013.01); *G09B 19/00* (2013.01); *G06T 2207/30242* (2013.01)

(58) Field of Classification Search
CPC ..................... G06T 7/0012; G06T 3/40; G06T 2207/30242; A61B 5/4088; G06K 9/6261; G06K 9/6262; G06K 9/628; G06K 9/6287; G09B 19/00
See application file for complete search history.

(56) References Cited

U.S. PATENT DOCUMENTS

| | | | | |
|---|---|---|---|---|
| 6,631,210 | B1 * | 10/2003 | Mutoh | H04N 1/40062 358/1.9 |
| 2011/0175916 | A1 * | 7/2011 | Noris | G06K 9/00416 345/441 |
| 2012/0134576 | A1 * | 5/2012 | Sharma | G06K 9/6249 382/155 |
| 2018/0060744 | A1 * | 3/2018 | Achin | G06N 5/02 |

* cited by examiner

*Primary Examiner* — Edward Martello
(74) *Attorney, Agent, or Firm* — Quarles & Brady LLP (57) ABSTRACT

Systems and methods of the present invention provide for: receiving a digital image data; modifying the digital image data to reduce a width of a feature within the digital image data; executing a dimension reduction process on the feature; storing a feature vector comprising: at least one feature for each of the received digital image data, and a correct or incorrect label associated with each feature vector; selecting the feature vector from a data store; training a classification software engine to classify each feature vector according to the label; classifying the image data as correct or incorrect according to a classification software engine; and generating an output labeling a second digital image data as correct or incorrect.

16 Claims, 6 Drawing Sheets

AUTOMATIC GRAPH SCORING FOR NEUROPSYCHOLOGICAL ASSESSMENTS

CROSS-REFERENCE TO RELATED APPLICATIONS

This application is a continuation of U.S. patent application Ser. No. 16/373,079 entitled "AUTOMATIC GRAPH SCORING FOR NEUROPSYCHOLOGICAL ASSESSMENTS" and filed on Apr. 2, 2019, which is a continuation of U.S. Provisional Patent Application No. 62/651,472 entitled "AUTOMATIC GRAPH SCORING FOR NEUROPSYCHOLOGICAL ASSESSMENTS" and filed on Apr. 2, 2018.

FIELD OF THE INVENTION

This disclosure relates to the field of automated neuropsychological assessments, and specifically systems and methods configured to automatically and efficiently score graph-based neuropsychological memory tests without human input.

SUMMARY OF THE INVENTION

The present invention provides systems and methods comprising one or more server hardware computing devices or client hardware computing devices, communicatively coupled to a network, and each comprising at least one processor executing specific computer-executable instructions within a memory that, when executed, cause the system to: receive a digital image data; modifying the digital image data to reduce a width of a feature within the digital image data; execute a dimension reduction process on the feature; store a feature vector comprising: at least one feature for each of the received digital image data, and a correct or incorrect label associated with each feature vector; select the feature vector from a data store; train a classification software engine to classify each feature vector according to the label; classify the image data as correct or incorrect according to a classification software engine; and generate an output labeling a second digital image data as correct or incorrect.

The above features and advantages of the present invention will be better understood from the following detailed description taken in conjunction with the accompanying drawings.

DETAILED DESCRIPTION

The present inventions will now be discussed in detail with regard to the attached drawing figures that were briefly described above. In the following description, numerous specific details are set forth illustrating the Applicant's best mode for practicing the invention and enabling one of ordinary skill in the art to make and use the invention. It will be obvious, however, to one skilled in the art that the present invention may be practiced without many of these specific details. In other instances, well-known machines, structures, and method steps have not been described in particular detail in order to avoid unnecessarily obscuring the present invention. Unless otherwise indicated, like parts and method steps are referred to with like reference numerals.

Figure 4:
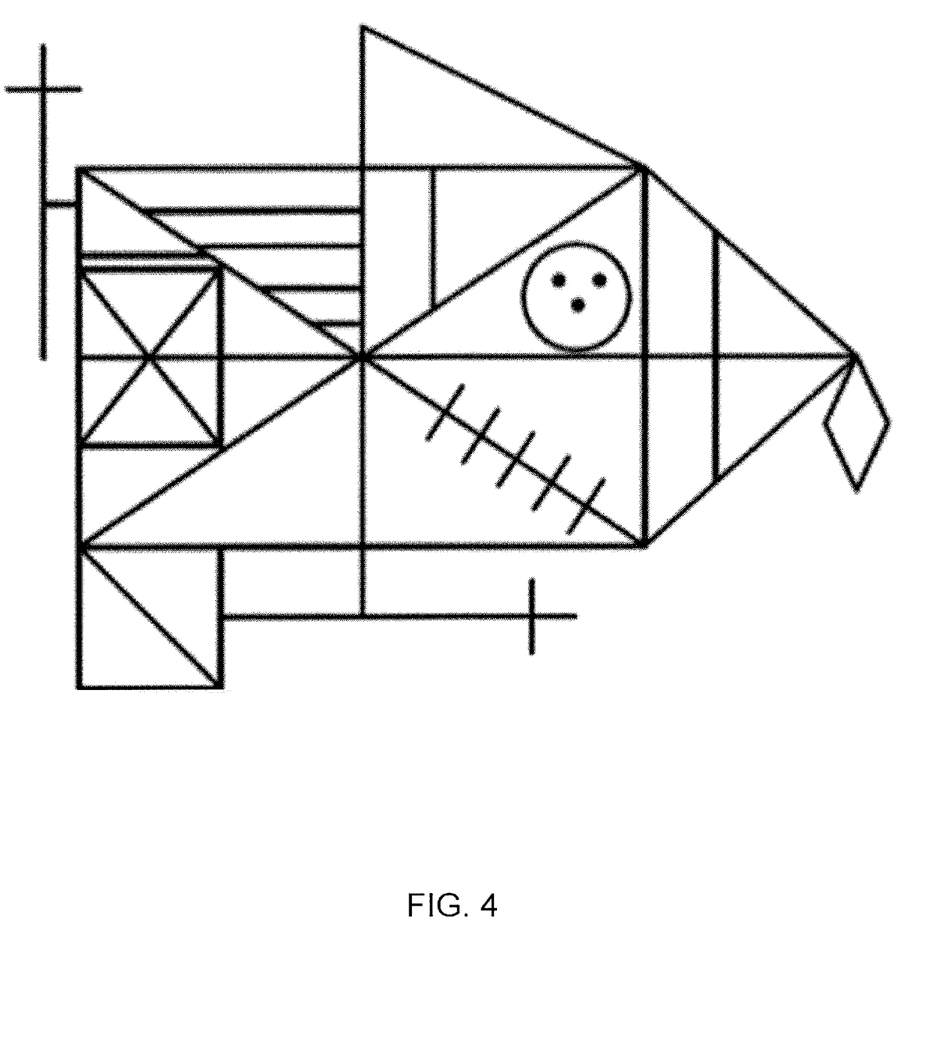
FIG. 4 illustrates a non-limiting example of a graph-based assessment tool used in the Rey Osterrieth Complex Figure (ROCF) neuropsychological assessment.

In neuropsychological assessments, clinicians may use graph-based tests to measure the functions or impairment of the cognitive ability of a patient. For example, such tests may include memory test scenarios, where a patient is shown a picture, graph, or other image for a certain period of time, and asked to draw the graph. More specifically, the clinician may show one or more pictures, graphs, and/or drawings to the patient, which may be as simple as a rectangle or circle, or may be more complicated, possibly including multiple combinations of different elements such as dots, lines, circles, etc. as seen in FIG. 4. After attempting to memorize the details of forms and/or shapes within the picture, the patient then tries to draw (e.g., using pen and paper) or otherwise recreate them (e.g., using a finger or stylus on the screen of a mobile device, and/or a mouse controlling a GUI).

Popular graph-based assessment tools include the Repeatable Battery for the Assessment of Neuropsychological Status (RBANS), the Wechsler Memory Scale (WMS), and the Rey Osterrieth Complex Figure (ROCF) (an example of which is seen in FIG. 4), among others. Once the patient has attempted to re-create the picture(s), the clinician may score the user generated graphs based on standard rubrics. The rubrics vary on different tests, but generally include checking the completeness of every element, the properties of the element (e.g., "whether a line is straight and horizontal"), and relative properties (e.g., "this element should be inside of that one"), etc.

As a non-limiting example, the test item "RECTANGLE" in an RBANS test includes rubrics given in extensive detail. These RECTANGLE rubrics may include the following non-limiting example checkpoints: 1) the lines of the rectangle must be unbroken and straight; 2) each interior angle must be approximately 90 degrees; 3) none of the interior angles may be less than 75 degrees; 4) top and bottom lines of the rectangle must be at least 25% longer than the sides of the rectangle; 5) the lines in the rectangle must not be rotated by more than 15 degrees; 6) the diagonal cross lines must be unbroken and straight; 7) two lines should approximately bisect each other; and 8) the ends of the lines should meet the corners of the rectangle without significant overlap or measurable distance between the ends of the lines and the corners.

Scoring these graphs using the appropriate rubrics is a labor and time intensive process, requiring the clinician to spend several hours (depending on the graphs and rubrics) measuring and calculating the accuracy of every feature, element, property, etc., then summarizing and finalizing the results into a comprehensive detailed and overall score for each drawing. In practice, several factors may also be introduced, which make the final score more arbitrary. For example, additional movements created according to the patient's motor control (which is generally regarded as acceptable) may create additional variations and arbitrariness in the scoring. Thresholds for "significant" or "measurable" parameters used to identify correct or incorrect grading according to rubrics may create additional disagreement among human graders, introducing vague or arbitrary scoring based on the required human judgement, which may also require additional time.

The current state of the art in the neuropsychological testing field does not address the inefficiencies and challenges of reading, analyzing, or scoring such tests. An automatic scoring system for these tests is therefore needed, which automates the scoring process, and overcomes the challenges from variations and human judgement.

The disclosed embodiments provide a system, and associated method steps, allowing clinicians to automate the neuropsychological assessment administration and scoring process described above, and receive near-instant automatic scoring for such graph-based tests using machine learning techniques to assess and to recognize shapes or other parameters within graphs received from users. Using this data, the disclosed embodiments automatically generate a score by applying the machine learning techniques trained by a collection of previously received input.

To accomplish this, the disclosed system receives a digital image/graph file as input, and executes the calculations and software logic described herein. As non-limiting examples, the disclosed system may receive one or more digital images or graphs as a scan of user input via a digital camera or scanner, or may receive input directly via a computer mouse, tactile input from a tablet, etc. Associated scoring data may also be received, indicating whether the re-creation of a displayed graph was correct or incorrect. The labels/scores may have been input by clinicians or other humans, possibly as evaluated and/or scored as being correctly or incorrectly labeled recreations of the original picture and/or included shapes. The disclosed system may then normalize the size and/or color of the digital image into a standard format, and clean or otherwise correct any errant data (e.g., stray marks).

After normalizing the input, the disclosed system may execute a "thinning" step, which attempts to modify the original input (e.g., the received digital image) to include only basic concise lines representing the most fundamental shape and/or structure of the received digital drawing data.

After completing the thinning process, the disclosed system may execute a dimension reduction process, possibly in the form of Principal Component Analysis (PCA). This process executes an orthogonal transformation to decrease the feature data within the file in order to decrease the size of the file itself, while maintaining the quality of the representation of the originally received digital image. The disclosed system then stores, within one or more data stores, the processed image data as feature vectors, associated scores and/or labels as correct or incorrect, and/or any other associated data associated with the received image.

The stored image data (i.e., the stored feature vector data, labels/scores, and any related data) may then be used as input to train a machine learning classification software engine to classify each feature vector for each digital image according to the label for each received digital image data, then classify and score/label any future received digital image data as correct or incorrect.

To train the machine learning classification software engine, the disclosed system may access the data stores and select the feature vector data for one or more previously-received digital images, processed according to the steps above. The feature vector data may include feature vectors and graded input in the form of labels and/or scores from previously-received digital image data. The disclosed machine learning process may use the plurality of previously received and graded data as a data pipeline, which is used as training data and/or models for training the machine learning classification software engine. In some embodiments, this software engine may utilize a Support Vector Machine (SVM—a non-limiting example of the classification software engine described herein) to score the basic graph elements and/or pixels from the digital image (stored as the feature vector data for the digital image in the disclosed embodiments), identifying the graph elements or pixels as correct or incorrect.

A nonlinear kernel with a Radial Basis Function (RBF) method (as a non-limiting example) may be used to train the classification software engine (e.g., the SVM) using the feature vector data from the basic graph elements or pixels that make up a training data.

The disclosed embodiments may then receive a new graph input file (e.g., digital image data) for analysis and, based on the machine learning applied to the feature vector data generated from the previously received digital image data, may use the classification software engine to automatically predict and/or generate a correct or incorrect label or score for the new graph input files, thereby automating the scoring of the tests received after the originally-received digital image data.

Figure 1:
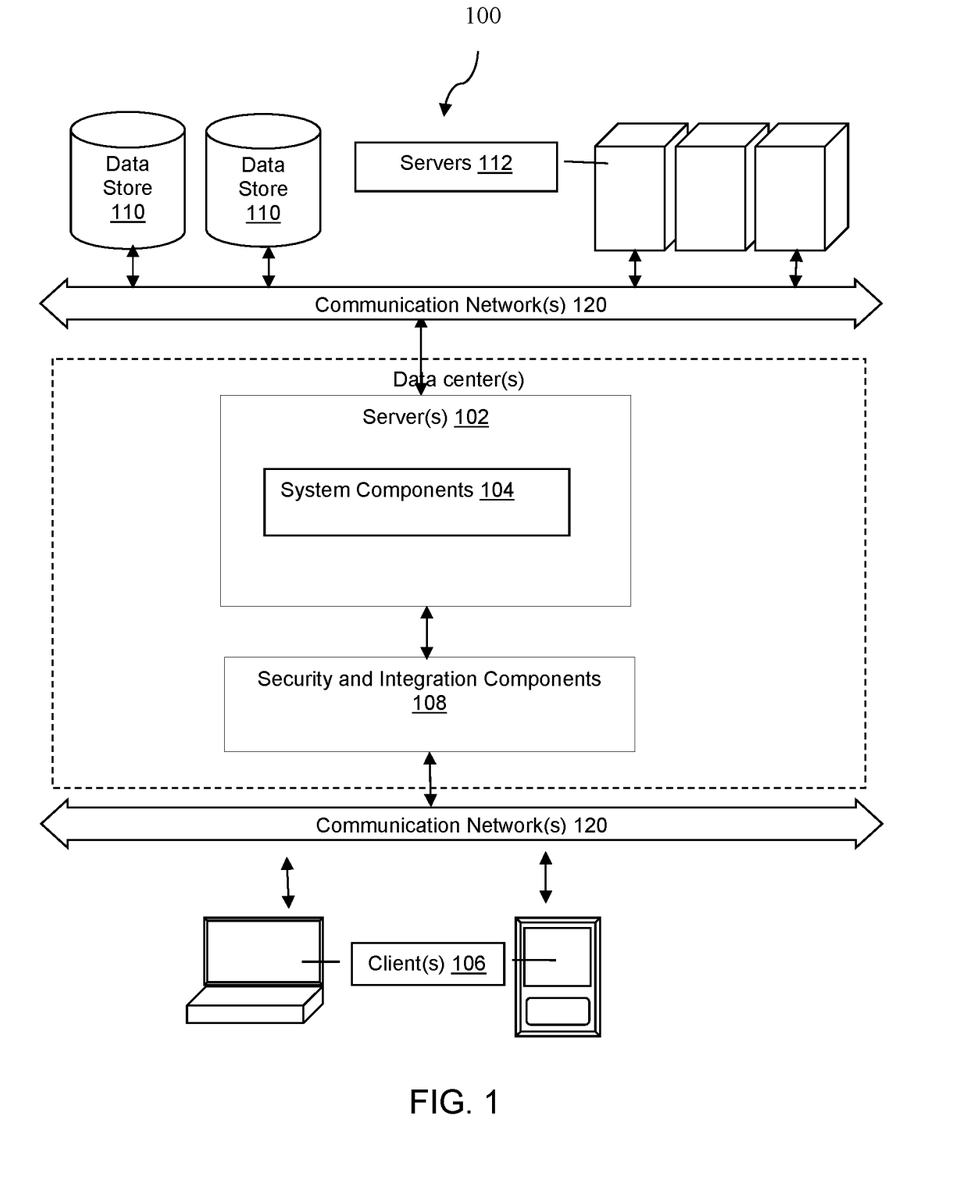
FIG. 1 illustrates a system level block diagram for an example embodiment of a system including the servers, clients, data stores, and network, configured for automatic graph scoring for neuropsychological assessments.

FIG. 1 illustrates a non-limiting example distributed computing environment 100, which includes one or more computer server computing devices 102, one or more client computing devices 106, and other components that may implement certain embodiments and features described herein. Other devices, such as specialized sensor devices, etc., may interact with client 106 and/or server 102. The server 102, client 106, or any other devices may be configured to implement a client-server model or any other distributed computing architecture.

Server 102, client 106, and any other disclosed devices may be communicatively coupled via one or more communication networks 120. Communication network 120 may be any type of network known in the art supporting data communications. As non-limiting examples, network 120 may be a local area network (LAN; e.g., Ethernet, Token-Ring, etc.), a wide-area network (e.g., the Internet), an infrared or wireless network, a public switched telephone networks (PSTNs), a virtual network, etc. Network 120 may use any available protocols, such as (e.g., transmission control protocol/Internet protocol (TCP/IP), systems network architecture (SNA), Internet packet exchange (IPX), Secure Sockets Layer (SSL), Transport Layer Security (TLS), Hypertext Transfer Protocol (HTTP), Secure Hypertext Transfer Protocol (HTTPS), Institute of Electrical and Electronics (IEEE) 802.11 protocol suite or other wireless protocols, and the like.

The subsystems and components within the server 102 and client devices 106 may be implemented in hardware, firmware, software, or combinations thereof. Various different subsystems and/or components 104 may be implemented on server 102. Users operating the client devices 106 may initiate one or more client applications to use services provided by these subsystems and components. Various different system configurations are possible in different distributed computing systems 100 and content distribution networks. Server 102 may be configured to run one or more server software applications or services, for example, web-based or cloud-based services, to support content distribution and interaction with client devices 106. Users operating client devices 106 may in turn utilize one or more client applications (e.g., virtual client applications) to interact with server 102 to utilize the services provided by these components. Client devices 106 may be configured to receive and execute client applications over one or more networks 120. Such client applications may be web browser based applications and/or standalone software applications, such as mobile device applications. Client devices 106 may receive client applications from server 102 or from other application providers (e.g., public or private application stores).

As shown in FIG. 1, various security and integration components 108 may be used to manage communications over network 120 (e.g., a file-based integration scheme or a service-based integration scheme). Security and integration components 108 may implement various security features for data transmission and storage, such as authenticating users or restricting access to unknown or unauthorized users, As non-limiting examples, these security components 108 may comprise dedicated hardware, specialized networking components, and/or software (e.g., web servers, authentication servers, firewalls, routers, gateways, load balancers, etc.) within one or more data centers in one or more physical location and/or operated by one or more entities, and/or may be operated within a cloud infrastructure.

In various implementations, security and integration components 108 may transmit data between the various devices in the content distribution network 100. Security and integration components 108 also may use secure data transmission protocols and/or encryption (e.g., File Transfer Protocol (FTP), Secure File Transfer Protocol (SFTP), and/or Pretty Good Privacy (PGP) encryption) for data transfers, etc.).

In some embodiments, the security and integration components 108 may implement one or more web services (e.g., cross-domain and/or cross-platform web services) within the content distribution network 100, and may be developed for enterprise use in accordance with various web service standards (e.g., the Web Service Interoperability (WS-I) guidelines). For example, some web services may provide secure connections, authentication, and/or confidentiality throughout the network using technologies such as SSL, TLS, HTTP, HTTPS, WS-Security standard (providing secure SOAP messages using XML encryption), etc. In other examples, the security and integration components 108 may include specialized hardware, network appliances, and the like (e.g., hardware-accelerated SSL and HTTPS), possibly installed and configured between servers 102 and other network components, for providing secure web services, thereby allowing any external devices to communicate directly with the specialized hardware, network appliances, etc.

Computing environment 100 also may include one or more data stores 110, possibly including and/or residing on one or more back-end servers 112, operating in one or more data centers in one or more physical locations, and communicating with one or more other devices within one or more networks 120. In some cases, one or more data stores 110 may reside on a non-transitory storage medium within the server 102. In certain embodiments, data stores 110 and back-end servers 112 may reside in a storage-area network (SAN). Access to the data stores may be limited or denied based on the processes, user credentials, and/or devices attempting to interact with the data store.

Figure 2:
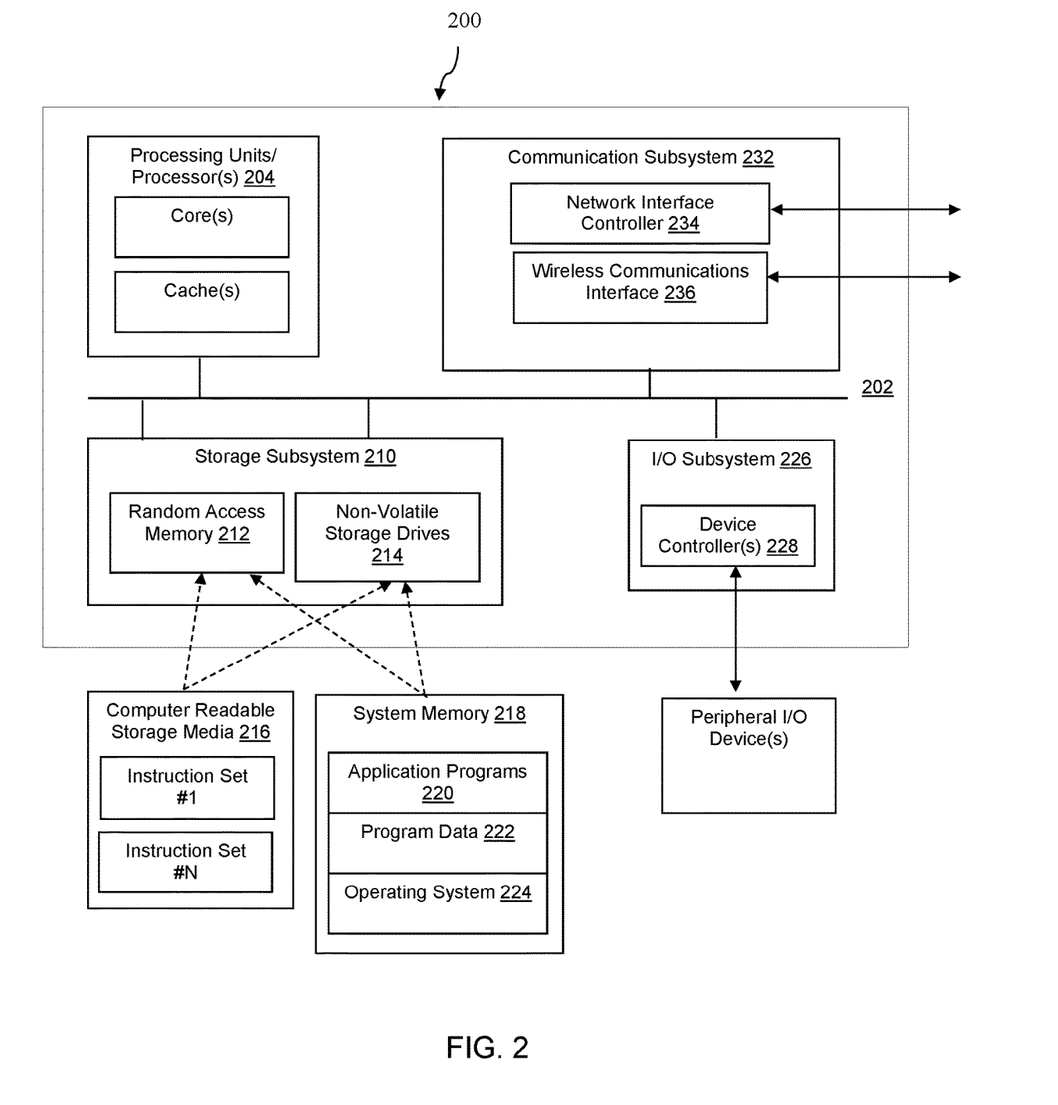
FIG. 2 illustrates a system level block diagram for an example embodiment of including a more detailed view of the components of each computing device within a system for automatic graph scoring for neuropsychological assessments.

With reference now to FIG. 2, a block diagram of an illustrative computer system is shown. The system 200 may correspond to any of the computing devices or servers of the network 100, or any other computing devices described herein. In this example, computer system 200 includes processing units 204 that communicate with a number of peripheral subsystems via a bus subsystem 202. These peripheral subsystems include, for example, a storage subsystem 210, an I/O subsystem 226, and a communications subsystem 232.

One or more processing units 204 may be implemented as one or more integrated circuits (e.g., a conventional microprocessor or microcontroller), and controls the operation of computer system 200. These processors may include single core and/or multicore (e.g., quad core, hexa-core, octo-core, ten-core, etc.) processors and processor caches. These processors 204 may execute a variety of resident software processes embodied in program code, and may maintain multiple concurrently executing programs or processes. Processor(s) 204 may also include one or more specialized processors, (e.g., digital signal processors (DSPs), outboard, graphics application-specific, and/or other processors).

Bus subsystem 202 provides a mechanism for intended communication between the various components and subsystems of computer system 200. Although bus subsystem 202 is shown schematically as a single bus, alternative embodiments of the bus subsystem may utilize multiple buses. Bus subsystem 202 may include a memory bus, memory controller, peripheral bus, and/or local bus using any of a variety of bus architectures (e.g. Industry Standard Architecture (ISA), Micro Channel Architecture (MCA), Enhanced ISA (EISA), Video Electronics Standards Association (VESA), and/or Peripheral Component Interconnect (PCI) bus, possibly implemented as a Mezzanine bus manufactured to the IEEE P1386.1 standard).

I/O subsystem 226 may include device controllers 228 for one or more user interface input devices and/or user interface output devices, possibly integrated with the computer system 200 (e.g., integrated audio/video systems, and/or touchscreen displays), or may be separate peripheral devices which are attachable/detachable from the computer system 200. Input may include keyboard or mouse input, audio input (e.g., spoken commands), motion sensing, gesture recognition (e.g., eye gestures), etc.

As non-limiting examples, input devices may include a keyboard, pointing devices (e.g., mouse, trackball, and associated input), touchpads, touch screens, scroll wheels, click wheels, dials, buttons, switches, keypad, audio input devices, voice command recognition systems, microphones, three dimensional (3D) mice, joysticks, pointing sticks, gamepads, graphic tablets, speakers, digital cameras, digital camcorders, portable media players, webcams, image scanners, fingerprint scanners, barcode readers, 3D scanners, 3D printers, laser rangefinders, eye gaze tracking devices, medical imaging input devices, MIDI keyboards, digital musical instruments, and the like.

In general, use of the term "output device" is intended to include all possible types of devices and mechanisms for outputting information from computer system 200 to a user or other computer. For example, output devices may include one or more display subsystems and/or display devices that visually convey text, graphics and audio/video information (e.g., cathode ray tube (CRT) displays, flat-panel devices, liquid crystal display (LCD) or plasma display devices, projection devices, touch screens, etc.), and/or non-visual displays such as audio output devices, etc. As non-limiting examples, output devices may include, indicator lights, monitors, printers, speakers, headphones, automotive navigation systems, plotters, voice output devices, modems, etc.

Computer system 200 may comprise one or more storage subsystems 210, comprising hardware and software components used for storing data and program instructions, such as system memory 218 and computer-readable storage media 216.

System memory 218 and/or computer-readable storage media 216 may store program instructions that are loadable and executable on processor(s) 204. For example, system memory 218 may load and execute an operating system 224, program data 222, server applications, client applications 220, Internet browsers, mid-tier applications, etc.

System memory 218 may further store data generated during execution of these instructions. System memory 218 may be stored in volatile memory (e.g., random access memory (RAM) 212, including static random access memory (SRAM) or dynamic random access memory (DRAM)). RAM 212 may contain data and/or program modules that are immediately accessible to and/or operated and executed by processing units 204.

System memory 218 may also be stored in non-volatile storage drives 214 (e.g., read-only memory (ROM), flash memory, etc.) For example, a basic input/output system (BIOS), containing the basic routines that help to transfer information between elements within computer system 200 (e.g., during start-up) may typically be stored in the non-volatile storage drives 214.

Storage subsystem 210 also may include one or more tangible computer-readable storage media 216 for storing the basic programming and data constructs that provide the functionality of some embodiments. For example, storage subsystem 210 may include software, programs, code modules, instructions, etc., that may be executed by a processor 204, in order to provide the functionality described herein. Data generated from the executed software, programs, code, modules, or instructions may be stored within a data storage repository within storage subsystem 210.

Storage subsystem 210 may also include a computer-readable storage media reader connected to computer-readable storage media 216. Computer-readable storage media 216 may contain program code, or portions of program code. Together and, optionally, in combination with system memory 218, computer-readable storage media 216 may comprehensively represent remote, local, fixed, and/or removable storage devices plus storage media for temporarily and/or more permanently containing, storing, transmitting, and retrieving computer-readable information.

Computer-readable storage media 216 may include any appropriate media known or used in the art, including storage media and communication media, such as but not limited to, volatile and non-volatile, removable and non-removable media implemented in any method or technology for storage and/or transmission of information. This can include tangible computer-readable storage media such as RAM, ROM, electronically erasable programmable ROM (EEPROM), flash memory or other memory technology, CD-ROM, digital versatile disk (DVD), or other optical storage, magnetic cassettes, magnetic tape, magnetic disk storage or other magnetic storage devices, or other tangible computer readable media. This can also include nontangible computer-readable media, such as data signals, data transmissions, or any other medium which can be used to transmit the desired information and which can be accessed by computer system 200.

By way of example, computer-readable storage media 216 may include a hard disk drive that reads from or writes to non-removable, nonvolatile magnetic media, a magnetic disk drive that reads from or writes to a removable, non-volatile magnetic disk, and an optical disk drive that reads from or writes to a removable, nonvolatile optical disk such as a CD ROM, DVD, and Blu-Ray® disk, or other optical media. Computer-readable storage media 216 may include, but is not limited to, Zip® drives, flash memory cards, universal serial bus (USB) flash drives, secure digital (SD) cards, DVD disks, digital video tape, and the like. Computer-readable storage media 216 may also include, solid-state drives (SSD) based on non-volatile memory such as flash-memory based SSDs, enterprise flash drives, solid state ROM, and the like, SSDs based on volatile memory such as solid state RAM, dynamic RAM, static RAM, DRAM-based SSDs, magneto-resistive RAM (MRAM) SSDs, and hybrid SSDs that use a combination of DRAM and flash memory based SSDs. The disk drives and their associated computer-readable media may provide non-volatile storage of computer-readable instructions, data structures, program modules, and other data for computer system 200.

Communications subsystem 232 may provide a communication interface from computer system 200 and external computing devices via one or more communication networks, including local area networks (LANs), wide area networks (WANs) (e.g., the Internet), and various wireless telecommunications networks. As illustrated in FIG. 2, the communications subsystem 232 may include, for example, one or more network interface controllers (NICs) 234, such as Ethernet cards, Asynchronous Transfer Mode NICs, Token Ring NICs, and the like, as well as one or more wireless communications interfaces 236, such as wireless network interface controllers (WNICs), wireless network adapters, and the like. Additionally and/or alternatively, the communications subsystem 232 may include one or more modems (telephone, satellite, cable, ISDN), synchronous or asynchronous digital subscriber line (DSL) units, Fire Wire® interfaces, USB® interfaces, and the like. Communications subsystem 236 also may include radio frequency (RF) transceiver components for accessing wireless voice and/or data networks (e.g., using cellular telephone technology, advanced data network technology, such as 3G, 4G or EDGE (enhanced data rates for global evolution), WiFi (IEEE 802.11 family standards, or other mobile communication technologies, or any combination thereof), global positioning system (GPS) receiver components, and/or other components.

In some embodiments, communications subsystem 232 may also receive input communication in the form of structured and/or unstructured data feeds, event streams, event updates, and the like, on behalf of one or more users who may use or access computer system 200. For example, communications subsystem 232 may be configured to receive data feeds in real-time from users of social networks and/or other communication services, web feeds such as Rich Site Summary (RSS) feeds, and/or real-time updates from one or more third party information sources (e.g., data aggregators). Additionally, communications subsystem 232 may be configured to receive data in the form of continuous data streams, which may include event streams of real-time events and/or event updates (e.g., sensor data applications, financial tickers, network performance measuring tools, clickstream analysis tools, automobile traffic monitoring, etc.). Communications subsystem 232 may output such structured and/or unstructured data feeds, event streams, event updates, and the like to one or more data stores that may be in communication with one or more streaming data source computers coupled to computer system 200.

The various physical components of the communications subsystem 232 may be detachable components coupled to the computer system 200 via a computer network, a Fire-Wire® bus, or the like, and/or may be physically integrated onto a motherboard of the computer system 200. Communications subsystem 232 also may be implemented in whole or in part by software.

Due to the ever-changing nature of computers and networks, the description of computer system 200 depicted in the figure is intended only as a specific example. Many other configurations having more or fewer components than the system depicted in the figure are possible. For example, customized hardware might also be used and/or particular elements might be implemented in hardware, firmware, software, or a combination. Further, connection to other computing devices, such as network input/output devices, may be employed. Based on the disclosure and teachings provided herein, a person of ordinary skill in the art will appreciate other ways and/or methods to implement the various embodiments. It should be noted that the embodiments shown in FIGS. 1-2 are examples of a distributed computing systems and are therefore not intended to be limiting.

Figure 3:
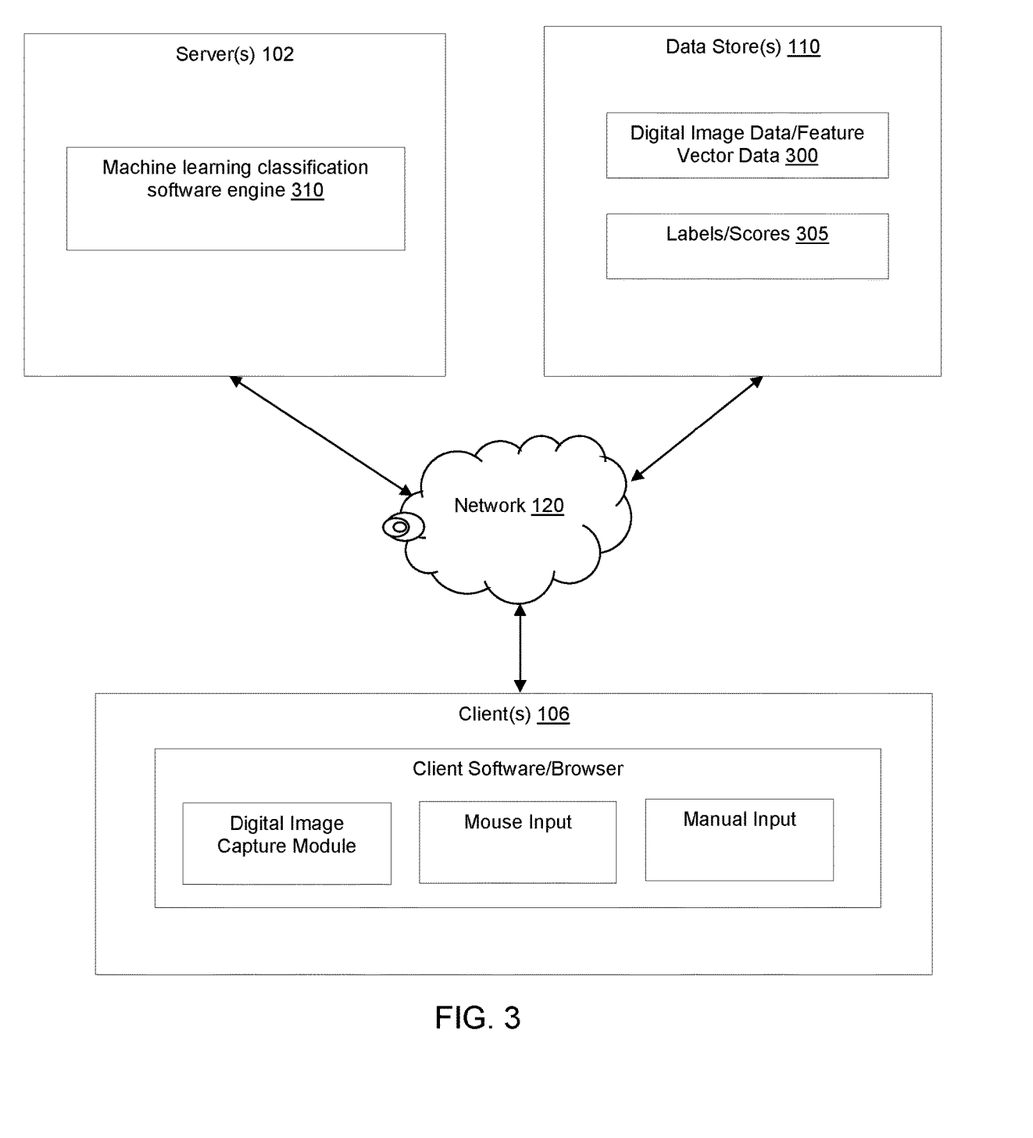
FIG. 3 illustrates a system level block diagram including a more detailed view of the servers, clients, and data stores within an example embodiment of a system for automatic graph scoring for neuropsychological assessments.

As shown in FIGS. 1-3, the disclosed embodiments provide a system comprising one or more servers 102, one or more clients 106 (or any other computing device), one or more data stores 110, and a communications network 120, the system being configured to automate the test scoring process described above. As in the original human-driven implementation of the test described above, the disclosed system captures raw user input. However, in the disclosed embodiments, the user input is captured in the form of a digital image recreating a displayed picture provided from the assessment.

Figure 5:
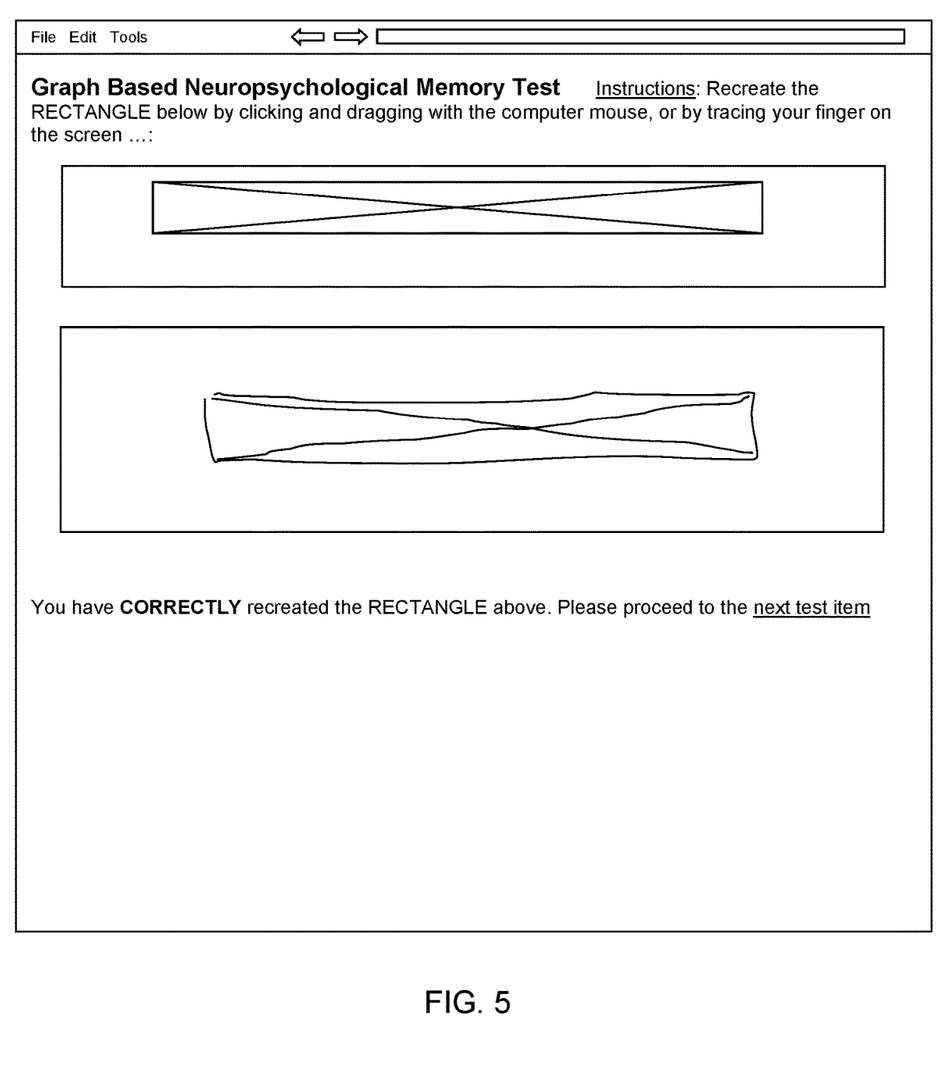
FIG. 5 illustrates a non-limiting example of a graphical user interface (GUI) within a system for automatic graph scoring for neuropsychological assessments.

In other words, for each test form on which to execute the calculations and software logic disclosed herein, clinicians or other workers may provide the patient or other test taker with an image to recreate, possibly by displaying the image on client 106, as seen in FIG. 5. Client 106 may receive input from the user, captured using any modality capable of capturing the image including, but not limited to: a digitized version of a physical drawing, captured via a digital camera or scanner, as non-limiting examples; mouse input from a mouse on a computer; manual input, such as fingers or a stylus on a tablet; etc. This user input is then transmitted to server 102 as digitized data.

Client 106 and/or server 102 may then process the input data, generating any digital image and/or image file known in the art. As non-limiting examples, the digital image/image file may comprise image and/or file data stored in a bitmap, PNG, JPEG, or any other known image file format. In some embodiments, the image may be captured and/or processed as a grayscale picture. The image may be processed and formatted to any size, including examples herein formatted within a 400×600 or 200×300 pixel image.

In some embodiments, client 106 and/or server 102 may capture additional data. For example, server 102 may receive a score and/or label, possibly designating the input digital image data as correct or incorrect, and may further capture examinee information specific to a system user, a timestamp for the time the test was taken, a timestamp reflecting when the image was entered, any additional user data or scoring data for the image, etc.

After capturing and receiving the digital image and any associated data, server 102 may automatically preprocess the captured digital image, with the goal of capturing the most correct image according to the intent of the user. This preprocessing may include cleaning and/or normalizing the digital image. As non-limiting examples, server 102 may correct or otherwise normalize the size and color of the digital image, possibly converting them into a standard format. Server 102 may further correct scratches, blemishes, or other anomalies within the digital image, which were not intended by the user, and may accommodate different modalities of the test (digital capture of paper/pencil images, etc.) without harm to the scoring performance.

Server 102 may further execute an additional step, referred to herein as "thinning," which attempts to modify the original input and received digital image to include only basic concise lines representing the most fundamental shape and/or structure of the received digital images. In some embodiments, server 102 may execute this as a pre-processing step.

Generally speaking, server 102 executes the thinning algorithm in order to decrease the width of one or more elements (e.g., lines that are larger or wider than the user intended) into very thin (e.g., 1-2 pixels), skeletal representations of each element in the received image data, without changing the fundamental structure or skeleton of the architecture of the original file. To accomplish this, server 102 may extract the key dots or pixels for every element (e.g., lines) or feature in the received digital image. The algorithm may include a mask or other map applied to each of the pixels within each of the elements, thereby possibly converting the digital image into a graph with a methodical analysis particularly focused on each pixel and/or cell within the arrangement of the mask or map.

In other embodiments, the digital image may be manipulated directly as a pixel matrix, since the image data is received as a pixel-based content. Server 102 may then analyze each specific pixel within the pixel based matrix, as well as each of the pixel's neighboring pixels. In other words, in embodiments where the received image is analyzed as a pixel matrix, server 102 may select a pixel within the pixel matrix (e.g., starting with the first pixel in the upper left of the pixel matrix), and make a determination whether each of the neighboring pixels (e.g., below, to the right of, and diagonal from the first pixel) include pixels within a color range for black, gray, or white pixels. After identifying each of the first pixel's neighbors as black, gray, or white pixels, logic for server 102 may identify the first pixel as black or white according to the neighboring pixels. As a simple example, server 102 may determine that each of the neighboring pixels are black, and because of this, the masking algorithm may dictate that the first pixel is also black. Similarly, server 102 may determine that each of the neighboring pixels are white, and that the first pixel is therefore also white.

However, if the neighboring pixels include some black pixels, some white pixels, and/or some pixels in a gray color range, logic within the masking algorithm may define a threshold above which the first pixel may be identified as a black pixel, and below which, the first pixel may be identified as a white pixel. Thus, if server 102 identifies the majority of neighboring pixels as black or within a darker gray color range (i.e., above the threshold), the first pixel may be identified as a black pixel. Conversely, if server 102 identifies the majority of neighboring pixels as white or within a lighter gray color range (i.e., below the threshold), the first pixel may be identified as a white pixel.

In addition to considering the immediate neighbors of the pixel under consideration, the disclosed embodiments also consider the pixels beyond those in contact with the first pixel. Consider the following example:

|    | y5 | y4 |    |
|----|----|----|----|
| x4 | x3 | x2 | y3 |
| x5 | p  | x1 | y2 |
| x6 | x7 | x8 | y1 |

In this example, if p is the pixel under consideration, the masking algorithm determines whether p is a black pixel or a white pixel not only according to those pixels immediately surrounding p (i.e., x1-x8), but also according to additional pixels more than one pixel away (e.g., y1-y5, as non-limiting examples). These pixels are not given equal weight to the pixels immediately neighboring the pixel under consideration.

After analysis of this first pixel and its neighbors, server 102 may move from the first pixel to a second pixel then perform the analysis below on this next pixel (e.g., the top pixel second from left in the matrix) and its neighbors. This analysis considers the identification of the first pixel as a black or white pixel as disclosed above when determining the color of the second pixel. After the second pixel is identified as a black or white pixel, the masking algorithm moves to the third pixel, and so on. The analysis may proceed through each pixel in the matrix until all have been analyzed as described herein.

From a more technical perspective, in the table seen above, point p will be deleted if G1: $X_h(p)=1$ G2: $2 \leq \min\{n_1(p), n_2(p)\} \leq 3$, where $n_{1(p)} = \Sigma_{i=1}^{4} x_{2k-1} \vee x_{2k}$, and $n_{2(p)} = \Sigma_{i=1}^{4} x_{2k} \vee x_{2k+1}$ represent the number of 4-adjacent pairs of pixels in N(P) containing one or two black pixels also, G3: $(x_2 \vee x_3 \vee (\sim x_3)) \wedge x_1 = 0$ in the first sub-iteration and 180° rotation in the second.

In other words, $X_h$ is the one function that checks each point. For criteria G1, $X_h(p)$ is the starting point for analyzing each of the plurality of pixel(s). If there is no information for G1/$X_h(p)$, that point/pixel is deleted, or in other words, set to 0.

G2 includes $n_{1(p)}$ and $n_{2(p)}$, which represent two combinations of those features relative to the pixel's neighbors, which takes into consideration four relative neighbors to determine if there is overlap (e.g., a number of 4-adjacent pairs of pixels in the N(P) containing one or two black pixels). If so, or if there is another connection between the pixel and the neighbors (e.g., minimum of 2 or 3 pixels sharing a connection), the analysis may determine that this is not a good representation of the neighbors, and these neighboring pixels may be deleted or set to 0.

Server 102 may attempt to reduce the size of the data being analyzed, possibly by performing a dimension reduction process to decrease the size of the input dimensions and/or the input features of the digital image data. In some embodiments, this may occur subsequent to the pre-processing steps disclosed above.

In practice, the utilized pixels within a graph derived from the digital image data are relatively sparse compared with the unutilized pixels in these images or photos. Because of this, dimension reduction may be utilized to pre-process and reduce the raw features of the digital image. Thus, the dimension reduction process may reduce the amount of data, possibly the amount of individual pixels for the received graph defined within the training data and/or feature vectors described below, into a smaller representation of the received digital file. Using an example of a long line within the digital image, the disclosed dimension reduction process may attempt to shrink the line into a more concise data.

In addition to decreasing the file size and the features within the file, the dimension reduction method may maintain the quality of the representation of the digital image data. As a non-limiting example, the dimension reduction method may be a PCA process. This PCA process may include less information, but may maintain as much data as is needed in this process in a more abbreviated form, while destroying unnecessary information, by executing an orthogonal transformation to decrease the feature data within the file in order to decrease the size of the file itself, while maintaining the quality of the representation of the originally received digital image.

Considering this issue from a pixel-based, rather than a feature-based perspective, a received 200*300 pixel digital image may include a very basic raw data sample including 60000 pixels in need of analysis, each of which may be considered a feature. This raw feature data represents a very large amount of data (specifically dimension data), which may be inefficient for server 102 to attempt to process in training an SVM model (described in more detail below). Even with extensive computing power, this type of increase in the dimensions of a sample data may require an exponentially increased amount of processing time and effort by server 102 in training one or more machine learning models.

As a solution to this problem, the dimension reduction method provides greater efficiency allowing server 102 to train and process machine learning models. Specifically, the PCA method of dimension reduction reduces the number of pixels considered in association with the received digital image, which, in turn, reduces the number of features considered in training the machine learning algorithm in classifying the digital image. This, in turn, reduces the size of the data into a high quality, but more compressed, representation or short form of the digital image feature data, which result in greater efficiencies for server 102, allowing server 102 to process the data to train the machine learning models based on the original digital image, while keeping the original data concise in a meaningful way.

As described in more detail below, Server 102 may use hyper parameters, applying different constraints, weights, or learning rates to different data patterns in a machine learning model, in order to "tune" (or choose a set of optimal hyper parameters for) the learning algorithm. These optimal hyper parameters may be used to decide the most efficient amount of pixel data output by the PCA process, in order to achieve the efficiency goals described above. As a non-limiting example, the hyper parameters may include the highest accuracy number of PCA components from 2-60000, with a selected level of 600, keeping more information with less data loss (there is loss, but the loss and gain efficiency is controlled in training), while increasing time to find the best model. This may achieve higher efficiency with lower effort in training the SVM.

From a more technical perspective, PCA is used to find the projection of data point $^{(i)}$ onto unit vector u. To maximize the variance of the projections, a unit length u may be chosen so as to maximize:

$$\frac{1}{m}\sum_{i=1}^{m}\left(x^{(i)T}u\right)^2 = \frac{1}{m}\sum_{i=1}^{m}u^T x^{(i)} x^{(i)T} u$$
$$= u^T\left(\frac{1}{m}\sum_{i=1}^{m}x^{(i)} x^{(i)T}\right)u.$$

Maximizing this subject to ||u||2=1 gives the principal eigenvector of, $$\sum = \frac{1}{m}\sum_{i=1}^{m}x^{(i)} x^{(i)T}$$

which is the empirical covariance matrix of the data. The selection of size has some effect on the final classification result.

Server 102 may then use an SVM or other classification software engine 310, to classify the received digital image data according to the labels 305 associated with a plurality of feature vectors 300 for previously-analyzed digital image data. Although SVM is the machine learning technique used in the disclosed embodiments due to the robust nature of its margins in using the supporting vectors to find the optimal decision, this non-limiting machine learning technique in no way limits the disclosed embodiments. Any known machine learning techniques (e.g., random forest models) could also be used to perform the disclosed method steps.

The disclosed SVM may include learning models with associated learning algorithms that analyze data used for classification and regression analysis. Given a set of training examples, each marked as belonging to one or the other of two categories (e.g., correct or incorrect in the disclosed non-limiting examples), an SVM training algorithm may build a model that assigns new examples to one category or the other, making it a non-probabilistic binary linear classifier.

An SVM model is a representation of the training examples, mapped so that the training examples of the separate categories are divided by a clear gap that is as wide as possible. New examples are then mapped and predicted to belong to a category based on which side of the gap they fall. SVMs can efficiently perform both linear and non-linear classification using a kernel (described in more detail below).

Thus, after the dimensions and other data have been reduced and the PCA outputs the reduced data (e.g., 600 pixels/features), the reduced data is input into the SVM to train the machine learning algorithm, possibly similar to a deep neural net on a classification task (though graph matching could also be used). The methodology includes training the models to score the basic graph elements which, in turn may lay a foundation to deal with complex graphs that are a combination of basic elements.

As a non-limiting example and as described above, the received digital image may be a 200×300 pixel image, which is received, pre-processed (possibly including the thinning algorithm), and its dimensions reduced, according to the most efficient dimension reduction determined by hyper parameter optimization, to include 600 pixels, each of which may be considered a feature within the feature vector data associated with the label of "correct" or "incorrect" associated with the received digital image.

Thus, each received digital image may be the training data from which the feature vector data is derived. As noted above, these training set data samples may include a plurality of previously received and graded data as a data pipeline. A clinician, examiner, or other human evaluator may grade basic test items (e.g., a rectangle) as correct or incorrect recreations of the original display. The evaluator may then label the test items as correct or incorrect, or otherwise score and label the test items. The disclosed system may then use the labels 305 or other scoring as training data and/or models for the machine learning within the classification software engine 310.

Server 102 may then perform the thinning and dimension reduction and store each of the pixels from the training data as features within the feature vector for the received digital image, the feature vector being stored in association with the received score/label for the received digital image. This feature vector data for each of the digital images, as well as the associated labels and other data may then be used in training the machine learning (and classification, described in more detail below).

Server 102 may store and track hundreds or even thousands of training data files within data store(s) 110 in order to train the SVM. Each of these training data files may include feature vector data 300 derived from each received digital image data, as well as an associated evaluator label data 305 indicating whether the test item was correct or incorrect, which is stored in association with feature vector data 300 derived from the training data files. The SVM may then analyze these labels 305 from practice tests or other evaluations in order to learn from the human scores on this data. The data pipeline utilized by the SVM may therefore include training set data samples made up of a pipeline of graph-based neuropsychological test results, and the SVM may be trained by building a model from raw pixels, and further learning from the labels 305.

In the disclosed embodiments, the SVM uses the feature vector training data 300 to train the model with a nonlinear kernel. However, this nonlinear kernel should not limit the scope of the disclosed embodiments. Any kernel known in the art compatible with the disclosed embodiments may be used.

In machine learning, kernel methods are a class of algorithms (including both SVM and PCA disclosed above) for pattern analysis. The general task of pattern analysis is to find and study general types of relations (for example principal components, correlations, classifications, etc.) in datasets. For many algorithms that solve these tasks, the data in raw representation have to be explicitly transformed into feature vector representations via a user-specified feature map. However, kernel methods require only a user-specified kernel, which include kernel functions for graphs, images, as well as vectors. Any linear model can be turned into a non-linear model by applying the kernel method to the model: replacing its features (predictors) by a kernel function.

For example, the disclosed invention may utilize kernel methods such as a Radial Basis Function (RBF) model, a basic or generic SVM model, a random forest method, etc., to train the SVM. Use of the RBF kernel in the disclosed tasks, with $$K(x, z) = \exp\left(-\frac{1}{2\tau^2}\|x-z\|_2^2\right)$$

and with the empirical regularization risk into cost function:

$$J_\lambda(\alpha) = \frac{1}{m}\sum_{i=1}^{m}\left[1 - y^{(i)}K^{(i)T}\alpha\right]_+ + \frac{\lambda}{2}\alpha^T K\alpha,$$

All hyper-parameters may be tuned with a cross-validation process (described below).

Thus, the RBF model is used in the example embodiments, but should not in any way limit the scope of the invention. Any compatible kernel functions may be used.

To train with the non-linear RBF model kernel, a running prototype may be established. The machine learning model may require different constraints, weights, or learning rates to generalize different data patterns. The models in the disclosed embodiments may therefore be tuned, or fine-tuned, by choosing a set of optimal hyper parameters for a learning algorithm using hyper parameter optimization. This process may include finding multiple hyper parameters that yield an optimal model without data loss.

In the disclosed embodiments, the hyper parameter optimization may be performed via a grid search, which entails searching through a manually specified subset of the hyper parameter space of a learning algorithm.

In the disclosed embodiments, the grid search algorithm may be guided by a performance metric via cross validation of the training set, and/or evaluation of a validation set. This cross-validation may combine and/or average measures of fit and/or prediction error to derive a more accurate estimate of model prediction performance.

The cross validation may include a model validation technique for assessing how the results of a statistical analysis will generalize to an independent data set, with the goal of estimating how accurately a predictive model will perform in practice. The model may therefore be given a training dataset of known data on which training is run, and a validation or training dataset of unknown data against which the model is tested. The goal of cross validation is to define a dataset to "test" the model in the training phase (i.e., the validation set), in order to give an insight on how the model will generalize to an independent dataset (i.e., an unknown dataset, e.g., from a real problem), etc.

One round of cross-validation involves partitioning a sample of data into complementary subsets, performing the analysis on one subset, the training set, and validating the analysis on the other subset, the validation set or testing set. To reduce variability, in most methods multiple rounds of cross-validation are performed using different partitions, and the validation results are combined (e.g. averaged) over the rounds to estimate a final predictive model.

As a non-limiting example, the disclosed embodiments may identify and tune the optimal hyper parameters (e.g., the best value for a number of features/components) for one or more models, without data loss, by performing a grid search algorithm via a 5 fold cross validation process.

The 5 fold cross validation process may include dividing the previously received digital image data/feature vector data 300, as well as their associated labels/scores 305 into 5 partitions, or folds. Four of these partitions may comprise the training dataset, and the fifth partition or fold may comprise the validation dataset. A training run or performance analysis may be performed on the validation dataset, and the 5 partitions may be rearranged, so that a different partition becomes the validation set, and the original partition used as the validation set is now part of the training dataset. This process may be repeated, including a training run using each of the partitions as a validation dataset compared against each of the remaining partitions as the training dataset. The average of each performance analysis is calculated, and the best of the averages is selected representing the best combination of hyper parameters for use in the model.

Thus, hyper parameters may be found and applied using a cross validation process, which evaluates each of the models with different hyper parameters to identify and establish the best hyper parameter values. In the disclosed embodiments, an SVM classifier equipped with an RBF kernel has at least two hyper parameters that need to be tuned for good performance: a regularization constant C and a kernel hyper parameter. To perform a grid search, one selects a finite set of values for each. Final values may be selected by the average high accuracy of cross validation results. Consider the following example of cross validation results:

| Parameter | Search Range | Value |
| --- | --- | --- |
| Number of PCA components | 2-60000 | 600 |
| C in SVM | 0.001-100 | 1.5 |
| Gamma in SVM | 0.0001-100 | 0.0026 |

In this example, the number of PCA components is finally set to 600 in a grid search scope from 5 to 60000. This best value of the hyper parameter for the number components was determined by the cross-validation method, as 600 in the grid search scope from 5 to 60000, 600 was identified as the best value.

As seen in the examples of C in SVM and Gamma in SVM, the hyper parameter with a basic range can be, for example, a wide range. For example, C or Gamma hyper parameters within the SVM in this example may identify the number of PCA dimensions and/or the linear rate. It is noteworthy that although the value of hyper parameter C for the SVM looks to be relatively low (indicating a conservative model), this example is located in a very conservative or a very small range to be better conservative in this method. The hyper parameter tuning must therefore be careful to avoid making the SVM too aggressive in trying to find matches.

To summarize the SVM method steps, the core machine learning models are trained by extensive feature vector training data 300 associated with human ground-truth labels 305. For example, every data file may be converted into an array of 600 numbers, which are associated with a label for the feature vector training data 300. Once the training data for the SVM has been compiled and the SVM trained, the final step is to use these trained models and the final hyper parameters to predict the labels on the test set and report the accuracies listed. Consider the following non-limiting example and corresponding performance metrics:

|  | Predicted Value | |
| --- | --- | --- |
| Actual Label | 1 | 0 |
| 1 | 45 | 7 |
| 0 | 28 | 40 |

| Index | Value |
| --- | --- |
| Accuracy | 71% |
| Precision | 87% |
| Recall | 62% |

After the SVM has been trained, server 102 then attempts to classify new incoming digital images by using the SVM or other classification software engine 310 to classify the features of incoming digital images into a category, possibly labeling the new incoming digital images as a correct or incorrect, or providing a more detailed score.

Server 102 may receive a new digital image input file for analysis, possibly converting the digital image into a graph or other digital image data, as described above. One or more algorithms within the SVM machine learning classification engine may automatically mimic human-based scoring, creating a final output of a high level label as correct or incorrect for a specific input shape or other feature, according to the machine learning for the SVM based on the previous training data sets, as described above. Thus, the disclosed embodiments may take the graph file as input and automatically generate and/or predict a correct or incorrect label thereby automating the scoring of the test.

In more advanced embodiments, the machine learning classification software engine may evaluate, using models of analysis for every element (requiring a great deal more data to train the SVM), individual rubrics as compared to specific elements, including all elements in that file, and generate specific scores based on each of these specific elements.

Figure 6:
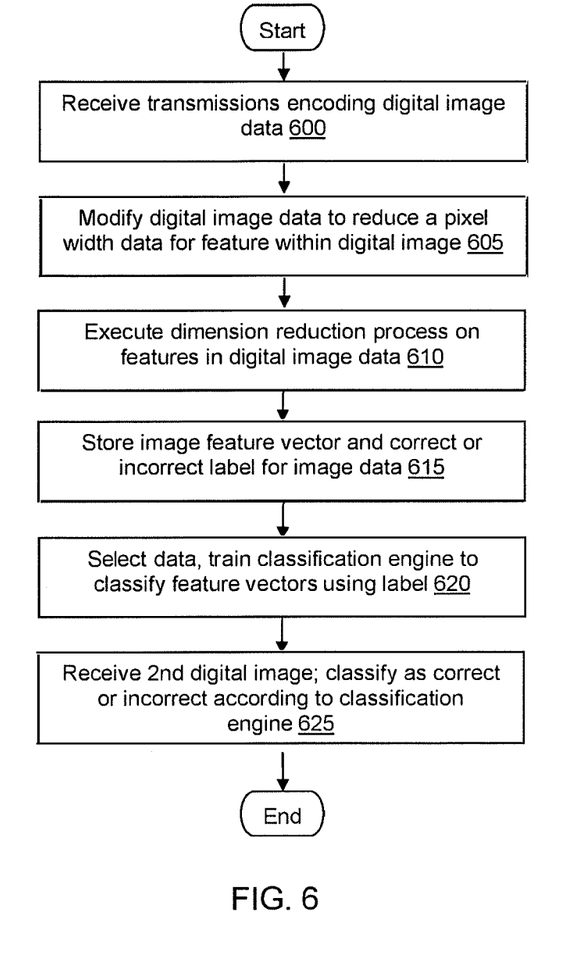
FIG. 6 illustrates a non-limiting example of a flow diagram representing the steps executed by the disclosed system for automatic graph scoring for neuropsychological assessments.

FIG. 6 includes a flowchart representing the method steps executed by the disclosed system. This system may include a server hardware computing device 102 coupled to a network and comprising at least one processor executing computer-executable instructions within a memory. In Step 600 the computer executable instructions cause the system to receive a plurality of transmissions, each encoding a digital image data. In step 605, server 102 modifies the digital image data to reduce a width of at least one feature within the digital image data. In step 610, server 102 executes a dimension reduction process on the at least one feature within the digital image data. In step 615, server 102 stores, within data store(s) 110: a feature vector for each digital image data in the plurality of transmissions, the feature vector comprising the at least one feature of the digital image; and a correct or incorrect label associated with each feature vector. In step 620, server 102 selects, from data store(s) 110, the feature vector for each digital image data, and trains a classification software engine to classify each feature vector according to the label associated with the feature vector. In step 625, server 102 receives a second transmission comprising a second digital image data; classify the second digital image data as correct or incorrect according to the classification software engine; and generate an output labeling the second digital image data as correct or incorrect.

In summary, the disclosed embodiments provide for the automation of the classification (and possibly scoring) of graph-based neuropsychological tests. These embodiments provide for the generation and aggregation of a pipeline of scored tests, used to train a machine learning model, which provides clinicians or other evaluators with instant automatic scoring of subsequent tests. The method steps in the disclosed embodiments may be instructions comprising specific device logic executed by a processor 204 on a server hardware computing device 112. The instructions may cause the disclosed system to execute the method steps disclosed herein.

As an initial step, server 112 may receive, through communication network(s) 120 one or more images or graph files, input by one or more users (such as test subjects, for example) and made up of digital image data representing the user's reproduction of a prompt for a graph-based neuropsychological test. The user may input the response directly, possibly using I/O devices and device controller(s) 228 within I/O subsystem 226, such as a mouse in a personal computer environment, or a stylus or finger in a mobile device environment. Server 112 may further receive the input by digital conversion of analog data, such as a scan or digital photograph of user input using other means. The evaluator (possibly a clinician assessing the reproduction by the user) may determine if the digital image data for the reproduction is correct or incorrect by applying one or more predetermined rubrics, and may input, into the disclosed system for storage (possibly using any combination of server 112, data store 110, and system components 104), a label identifying the reproduction as correct or incorrect.

The determination of a correct or an incorrect reproduction may be a subjective determination by the evaluator, according to predefined rubrics, as to whether the user has accurately reproduced the provided digital image. Continuing the non-limiting example above, the user may be provided with an image of a rectangle, and the evaluator may be provided with specific rubrics, such as unbroken lines, approximately 90 degree angles, etc., as outlined above. If the user has correctly reproduced the rectangle according to the provided rubrics, the evaluator may input, possibly using I/O subsystem 226, a label of correct for the digital image data. If not, the evaluator may input an incorrect label.

The system components 104 including processor 204 within server 112 may monitor the number of digital image data collections and associated labels received via I/O subsystem 226, and determine a threshold of digital image data and labels considered sufficient to train the disclosed machine learning algorithms. In some embodiments, the threshold for determining a sufficient number of digital image data and labels may be determined by comparing, possibly using processor 204 and other system components 104 within server 112, the number of features, described below, with the number of data samples received. The system may then determine that the closer the number of samples is to the number of features within each sample, the more likely that the threshold number has been reached.

After collecting a sufficient number of examples of digital image data and their accompanying labels as correct or incorrect, and storing the received data in association in data store 110, the processor 204 and other system components 104 in server 112 may train and apply core machine learning models, methods, functions, and/or algorithms, referred to herein as machine learning models or algorithms, to predict the classification of subsequent incoming user reproductions as correct or incorrect.

In order to create and train the machine learning model, the disclosed system may identify one or more features—individual measurable properties or characteristics of a phenomenon being observed, which are ultimately used for pattern recognition, classification, regression, etc., as described below. In the machine learning model in the disclosed embodiments, these features may include the pixels from the digital image data. As described in more detail below, processor 204 on server 112 may identify each pixel within the digital image data, and convert each pixel into a feature within a feature matrix, possibly as a numeric value representing the pixel as a feature, into a graph or a pixel matrix from the original reproduced image.

Processor 204 and system components 104 on server 112 may then transform each digital image data in raw representation into a feature vector, used to conveniently describe a set of numeric features, which may be compared to a defined threshold to determine a class for the feature vector, such as whether the reproduction represented by the feature vector is correct or incorrect. In some embodiments, the digital image data may be explicitly transformed into feature vector representations via a user-specified feature map. For example, processor 204 and system components 104 on server 112 may receive each pixel within each received digital image data and identify it as a data point or feature of the received image. The system 100 may transform each data point into a number (e.g., integer, float, double, etc.) so that each collection of digital image data may become an array of numbers representing each of the pixels. As a non-limiting example, after the dimension reduction described below, system 110 the features of each image may include an image vector of 600 numbers, each representing a pixel in the image.

Prior to the machine learning analysis, processor 204 and system components 104 on server 112 may apply several pre-processing steps to the received digital image data. For example, system 100 may normalize the input image data, including normalizing the size and color of the image data, into a standard format, deleting unnecessary information, such as scratches from scanning an image or blurs on a camera, for example.

Another preprocessing step, referred to as thinning herein, may modify the received image data (such as reducing any input lines to 1-2 pixels) by applying a map to isolate and extract the key pixels that represent the input image file without changing the structure of the original file. The system may use this thinning algorithm to decrease the total features in each feature vector.

For example, processor 204 and system components 104 on server 112 may reduce at least one feature within the digital image data by merging some of the pixels with their immediate neighbor pixels, in order to define the intended pixels or lines created by the user. If a user were to create an image with particularly thick lines, the number of relevant features within the feature vector would increase significantly, subjecting the data to the "curse of dimensionality" where the number of features within a particular dataset becomes unwieldy. The thinning process, therefore, would simplify and reduce the image data included within the thicker lines, generating image data based on lines that are no more than 1-2 pixels wide, thereby reducing the number of relevant features within the digital image data.

This process repeats for each pixel identified within the input digital image data. As each pixel is identified, processor 204 and system components 104 on server 112 further identify the pixels that are immediately adjacent to the identified pixel, determines whether the immediately adjacent pixels are black or white, and determines a total number of each, possibly identifying the white pixels as empty feature data. If the total number of black pixels is greater than a threshold number, or if a majority of the immediately adjacent pixels is black, system 100 may characterize the current pixel as a black pixel. If not, system 100 may characterize the pixel as a white pixel and/or empty feature data.

However, this process is not limited to the immediately adjacent pixels or features. Processor 204 and system components 104 on server 112 may analyze additional pixels beyond the current pixel's immediate neighbors, and determine whether the current pixel is black or white according to these additional pixels. The additional pixels or features may be weighted with less weight than the immediately adjacent pixels when analyzing the current pixel to determine whether it is black or white.

Another preprocessing step may include reducing the dimensions of the features from the digital image data, thereby avoiding the "curse of dimensionality," where the dimensions in a feature vector (i.e., the pixels from the digital image data) are too great to effectively analyze. As a non-limiting example, the captured image data may include a 400×600 pixel .bmp or .png file, which would include 240,000 features to analyze for each image data. Even a 200×300 pixel image would include 60,000 features, which would make training the machine learning algorithm (such as an SVM, described below) difficult. Instead, a dimension reduction algorithm may isolate the relevant features, thereby decreasing the time and effort needed to analyze the digital image data. For example, lines within the drawing may be reduced to more concise data, shrinking the number of features into a good representation while keeping the relevant information.

In some embodiments, processor 204 and system components 104 on server 112 executes the dimension reduction algorithm in the form of an orthogonal transformation to reduce a number of the at least one feature within the feature vector data for each digital image data. In some embodiments, the dimension reduction algorithm may be a Principal Component Analysis (PCA) algorithm, a machine learning model which uses a projection of a data point onto a unit vector in order to decrease the size of the features, while maintaining a concise representation of the digital image data.

The PCA model may include one or more hyper parameters. These hyper parameters represent the optimum number of output pixels determined to include the most relevant information. Processor 204 and system components 104 on server 112 may apply these hyper parameters to the machine learning algorithm, as parameters whose value is used to control the learning process, which require different constraints, weights, or learning rates to generalize the different data patterns in the machine learning algorithm.

System 100 may test these hyper parameters within a range, attempting to balance the maximum efficiency of time and resources needed for training the model, while retaining the maximum amount of information without control loss, thereby representing the optimal hyper parameters for the model. As a non-limiting example, the range of potential hyper parameters in some embodiments may include principal components in a range from 2 to 60000, based on a 200×300 pixel image, where 600 represented an optimal hyper parameter, or in other words, the optimal number of features, for the model.

System 100 may identify the optimal hyper parameters using cross-validation to identify and tune the hyper parameters, allowing the machine learning algorithms to optimally solve machine learning problems using optimal hyper parameters. In other words, the identification and tuning of the hyper parameters yields an optimal model which minimizes a predefined loss function when data is analyzed.

Processor 204 and system components 104 on server 112 may then grid-search or parameter sweep the hyper parameters, by exhaustively searching through a manually specified subset of the hyper parameter space of the learning algorithm, measured by cross-validation of a training set or evaluation on a held-out validation set. In other words, multiple iterations will be performed on each of the training sets, in order to train the machine learning algorithm, with each set identifying potential hyper parameters to be used in the machine learning algorithm. The held-out validation set may be used as a "control group" to validate the results of each of the training sets.

In some embodiments, the grid search is done by making a calculation from the original point and then evaluating the performance in order to select a direction in that search until a good minimum point with a highest accuracy on the training data is found. To accomplish this, in some embodiments, cross-validation may include partitioning feature vectors and/or other digital image data into a plurality of partitions. One of these partitions may be designated as the validation dataset. Each of the remaining datasets may then be designated as training datasets, which are used to train the PCA model. The system may then perform an analysis on each of the plurality of training subsets in the training datasets validating the analysis against the validation dataset. Processor 204 and system components 104 on server 112 may then repeat the performance analysis for each remaining partition, designating one of the folds as a validation dataset, and each remaining partition as a training dataset.

After completing the cross validation process, with each partition acting as both a validation set and a training dataset, system 100 may analyze the hyper parameter results for each of the runs and compile and compare the combinations of hyper parameters for each of the partitions. Processor 204 and system components 104 on server 112 may then average the performance of the hyper parameters within each of the partitions, and analyze different combinations of hyper parameters, selecting the best combination of the hyper parameters. Final values may then be selected by the average high accuracy of cross validation results, thereby concluding the grid search. As a non-limiting example, a 5-fold cross validation may be used to identify and tune the hyper parameters and train the model, where the feature vectors are separated into 5 partitions, with 1 validation dataset and 4 training datasets. The system may perform 5 runs, with each of the 5 folds acting as the validation dataset.

The output of the PCA process may be used as input to the classification software engine 310, and this input may be used to train the classification software engine 310 to classify subsequent incoming digital image data, and provide appropriate labels as correct or incorrect. Because the outputs of the incoming digital image data, specifically a classification including a correct or incorrect label, is restricted to a limited set of values, the classification software engine may utilize supervised learning algorithms.

Because the classification software engine 310 classifies images into labels by learning the human labels for the digital image data, in some embodiments, the classification software engine 310 may utilize Support Vector Machine (SVM) algorithms, which include supervised learning models with associated learning algorithms that analyze data used for classification and regression analysis. In some embodiments, the SVM uses machine learning to classify the digital image data according to provided labels where, given a set of training examples, each marked as belonging to one or the other of two categories (correct or incorrect), an SVM training algorithm builds a model that assigns new examples to one category or the other, making it a non-probabilistic binary linear classifier.

However, the disclosed embodiments are not limited to linear models or algorithms. In some embodiments, such as some embodiments using the SVM algorithms described herein, a non-linear Radial Basis Function (RBF) kernel method may be used to turn a linear model (e.g., a feature based approach) into a non-linear model, using the feature vector to train the model using the non-linear RBF approach. In machine learning, kernel methods are a class of algorithms for pattern analysis (e.g., classifications of data sets), such as the SVM algorithm described herein. Thus, kernels such as the RBF kernel may require only a user-specified kernel, rather than, or in addition to, utilizing a user-specified feature map.

The kernel algorithms may identify a principal eigenvector, which provides a covariance matrix of data that avoids overfitting data (allowing for little variance and therefore failing to consider data that should be considered), or under fitting data, which includes data that is not intended to be analyzed. For example, in analyzing a straight line input by a human, the eigenvector would provide for the human error in drawing less than a perfectly straight line.

Processor 204 and system components 104 on server 112 may train the classification software engine 310 to classify each feature vector according to the label associated with the feature vector. The classification software engine 310 may use machine learning method to predict a score for that graph, treating the scoring as a classification task to automate the classification of the feature vectors (or scoring of the test). In other words, the disclosed embodiments build a machine learning model from raw pixels by learning to classify the images according to human labeled scores.

To accomplish this, the classification software engine 310 may first train a machine learning algorithm using the existing digital image data, identifying and tuning hyper parameters using cross-validation methods similar to that described in association with the PCA algorithms above. System 100 may select the existing feature vectors (i.e., an array of numbers) for previously input and stored digital image data, along with each feature vector array's label as correct or incorrect. The system may then partition the feature vectors and/or other digital image data into a plurality of partitions or folds, as above. One of these partitions may be designated as the validation dataset. Each of the remaining datasets may then be designated as training datasets, which are used to train the SVM model. System 100 may then perform an analysis on each of the plurality of training subsets in the training datasets validating the analysis against the validation dataset. System 100 may then repeat the performance analysis for each remaining partition, designating one of the folds as a validation dataset, and each remaining partition as a training dataset.

After completing the cross validation process, with each partition acting as both a validation set and a training dataset, processor 204 and system components 104 on server 112 may analyze the classification hyper parameter results for each of the runs and compile and compare the combinations of classification hyper parameters for each of the partitions. System 100 may then average the performance of the classification hyper parameters within each of the partitions, and analyze different combinations of classification hyper parameters, selecting the best combination of the classification hyper parameters. Final values may then be selected by the average high accuracy of cross validation results. As a non-limiting example, a 5-fold cross validation may be used to identify and tune the classification hyper parameters and train the model, where the feature vectors are separated into 5 partitions, with 1 validation dataset and 4 training datasets. The system may perform 5 runs, with each of the 5 folds acting as the validation dataset.

The SVM model may then be trained using a final combination of classification hyper parameters, which are used to predict the labels for subsequent incoming digital image data and report the accuracies or any inaccuracies of the model.

Once the model is trained, the classification software engine 310 may receive a second image input comprising a second digital image data and, using the trained classification software engine 310 classify the second digital image data as correct or incorrect according to the trained machine learning model, and generate an output including a label for the second digital image data as correct or incorrect.

Other embodiments may be envisioned that use the disclosed systems and methods, as well as machine learning algorithms or deep neural networks, to identify, analyze, and score all shapes and drawings within a digital image data, and score each shape, or the digital image as a whole, according to a predefined set of rubrics.

Other embodiments and uses of the above inventions will be apparent to those having ordinary skill in the art upon consideration of the specification and practice of the invention disclosed herein. The specification and examples given should be considered exemplary only, and it is contemplated that the appended claims will cover any other such embodiments or modifications as fall within the true scope of the invention.

The Abstract accompanying this specification is provided to enable the United States Patent and Trademark Office and the public generally to determine quickly from a cursory inspection the nature and gist of the technical disclosure and in no way intended for defining, determining, or limiting the present invention or any of its embodiments.

The invention claimed is:

1. A system comprising a server, comprising a hardware computing device coupled to a network and including at least one processor executing instructions within a memory which, when executed, cause the system to:
   receive digital image data;
   for each of a first plurality of pixels within the digital image data:
      identify a pixel within the first plurality of pixels;
      identify a total number of black pixels within:
         a second plurality of pixels immediately adjacent to the pixel; and
         a third plurality of pixels immediately adjacent to the second plurality of pixels;
      determine whether the total number of black pixels is greater than a threshold number;
      responsive to a determination that the total number of black pixels is greater than the threshold number, characterize the pixel as a black pixel; and
      responsive to a determination that the total number of black pixels is not greater than the threshold number, characterize the pixel as a white pixel or an empty pixel.

2. The system of claim 1, wherein the instructions further cause the system to:
   receive a plurality of image inputs, wherein the digital image data is one of a plurality of image data, each digital image data being associated with one of the plurality of image inputs;
   execute a dimension reduction process on at least one feature within the digital image data;
   store, within a data store:
      a feature vector for each digital image data associated with each of the plurality of image inputs, the feature vector comprising the at least one feature of the digital image data; and
      a correct or incorrect label associated with each feature vector;
   select, from the data store, the feature vector for each digital image data; and
   train a classification software engine to classify each feature vector according to the label associated with the feature vector.

3. The system of claim 2, wherein the instructions further cause the system to:
   receive a second image input comprising a second digital image data;
   classify the second digital image data as correct or incorrect according to the classification software engine; and
   generate an output labeling the second digital image data as correct or incorrect.

4. The system of claim 2, wherein the instructions further cause the system to, for each of a first plurality of pixels within the digital image data:
   identify a pixel within the first plurality of pixels;
   identify a total number of black pixels within a second plurality of pixels immediately adjacent to the pixel and a third plurality of pixels immediately adjacent to the second plurality of pixels;
   determine whether the total number of black pixels is greater than a threshold number;
   responsive to a determination that the total number of black pixels is greater than the threshold number, characterize the pixel as a black pixel; and
   responsive to a determination that the total number of black pixels is not greater than the threshold number, characterize the pixel as a white or an empty pixel.

5. The system of claim 2, wherein the dimension reduction process includes execution of an orthogonal transformation to reduce a number of the at least one feature within the feature vector data for each digital image data.

6. The system of claim 2, wherein:
   each at least one feature is a pixel in the digital image data; and
   the dimension reduction algorithm reduces the number of pixels and features in the feature vector.

7. The system of claim 2, wherein the classification software engine uses the feature vector to train the model with a non-linear Radial Basis Function (RBF) kernel method.

8. The system of claim 2, wherein the classification software engine is trained by:
   partitioning the plurality of feature vectors into a plurality of folds;
   designating a fold within the plurality of folds as a validation dataset;
   designating each remaining fold in the plurality of folds as a training dataset;

running a performance analysis for each of a plurality of subsets in the training dataset, the performance analysis comprising:
performing an analysis on each of the plurality of training subsets in the training dataset; and
validating the analysis against the validation dataset;
designating each remaining fold in the plurality of folds as the validation dataset, and the validation dataset as being within the training dataset; and
repeating the performance analysis for each remaining fold in the plurality of folds.

9. A method comprising:
receiving, by a server comprising a hardware computing device coupled to a network and including at least one processor executing instructions within a memory, digital image data;
for each of a first plurality of pixels within the digital image data:
identifying, by the server, a pixel within the first plurality of pixels;
identifying, by the server, a total number of black pixels within:
a second plurality of pixels immediately adjacent to the pixel; and
a third plurality of pixels immediately adjacent to the second plurality of pixels;
determining, by the server, whether the total number of black pixels is greater than a threshold number;
responsive to a determination that the total number of black pixels is greater than the threshold number, characterizing, by the server, the pixel as a black pixel; and
responsive to a determination that the total number of black pixels is not greater than the threshold number, characterizing, by the server, the pixel as a white pixel or an empty pixel.

10. The method of claim 9, further comprising the steps of:
receiving, by the server, a plurality of image inputs, wherein the digital image data is one of a plurality of image data, each digital image data being associated with one of the plurality of image inputs;
executing, by the server, a dimension reduction process on at least one feature within the digital image data;
storing, by the server, within a data store:
a feature vector for each digital image data associated with each of the plurality of image inputs, the feature vector comprising the at least one feature of the digital image data; and
a correct or incorrect label associated with each feature vector;
selecting, by the server, from the data store, the feature vector for each digital image data; and
training, by the server, a classification software engine to classify each feature vector according to the label associated with the feature vector.

11. The method of claim 10, further comprising the steps of:
receiving, by the server, a second image input comprising a second digital image data;
classifying, by the server, the second digital image data as correct or incorrect according to the classification software engine; and
generating, by the server, an output labeling the second digital image data as correct or incorrect.

12. The method of claim 10, further comprising the steps of, for each of a first plurality of pixels within the digital image data:
identifying, by the server, a pixel within the first plurality of pixels;
identifying, by the server, a total number of black pixels within a second plurality of pixels immediately adjacent to the pixel and a third plurality of pixels immediately adjacent to the second plurality of pixels;
determining, by the server, whether the total number of black pixels is greater than a threshold number;
responsive to a determination that the total number of black pixels is greater than the threshold number, characterizing by the server, the pixel as a black pixel; and
responsive to a determination that the total number of black pixels is not greater than the threshold number, characterizing, by the server, the pixel as a white or an empty pixel.

13. The method of claim 10, wherein the dimension reduction process includes execution of an orthogonal transformation to reduce a number of the at least one feature within the feature vector data for each digital image data.

14. The method of claim 10, wherein:
each at least one feature is a pixel in the digital image data; and
the dimension reduction algorithm reduces the number of pixels and features in the feature vector.

15. The method of claim 10, wherein the classification software engine uses the feature vector to train the model with a non-linear Radial Basis Function (RBF) kernel method.

16. The method of claim 10, wherein the classification software engine is trained by:
partitioning, by the server, the plurality of feature vectors into a plurality of folds;
designating, by the server, a fold within the plurality of folds as a validation dataset;
designating, by the server, each remaining fold in the plurality of folds as a training dataset;
running, by the server, a performance analysis for each of a plurality of subsets in the training dataset, the performance analysis comprising:
performing an analysis on each of the plurality of training subsets in the training dataset; and
validating the analysis against the validation dataset;
designating, by the server, each remaining fold in the plurality of folds as the validation dataset, and the validation dataset as being within the training dataset; and
repeating, by the server, the performance analysis for each remaining fold in the plurality of folds.

* * * * *

UNITED STATES PATENT AND TRADEMARK OFFICE
CERTIFICATE OF CORRECTION

PATENT NO. : 11,580,636 B2
APPLICATION NO. : 16/953150
DATED : February 14, 2023
INVENTOR(S) : Zhaodong Wang It is certified that error appears in the above-identified patent and that said Letters Patent is hereby corrected as shown below:

In the Specification

Column 11, Line 38, "$\sum_{i=1}^{4}$" should be -- $\sum_{i=1}^{4}$ --.

Column 11, Line 39, "$\sum_{i=1}^{4}$" should be -- $\sum_{i=1}^{4}$ --.

Signed and Sealed this
Twelfth Day of September, 2023

Katherine Kelly Vidal
*Director of the United States Patent and Trademark Office*